United States Patent [19]

Gobbi

[11] Patent Number: 5,750,149
[45] Date of Patent: May 12, 1998

[54] PHARMACEUTICAL AND DERMOCOSMETIC COMPOSITIONS CONTAINING EQUINE COLOSTRUM

[75] Inventor: Rosa Maria Gobbi, Milan, Italy

[73] Assignee: Horse Vitality Ltd, Dublin, Ireland

[21] Appl. No.: 464,904

[22] PCT Filed: Dec. 22, 1993

[86] PCT No.: PCT/EP93/03655

§ 371 Date: Aug. 14, 1995

§ 102(e) Date: Aug. 14, 1995

[87] PCT Pub. No.: WO94/16675

PCT Pub. Date: Aug. 4, 1994

[30] Foreign Application Priority Data

Jan. 26, 1993 [IT] Italy .................... MI93A0118
Jul. 1, 1993 [IT] Italy .................... MI93A1417

[51] Int. Cl.⁶ .................... A61K 35/20

[52] U.S. Cl. .................... 424/535; 424/DIG. 13; 530/832

[58] Field of Search .................... 424/535, DIG. 13; 530/832

[56] References Cited

U.S. PATENT DOCUMENTS 4,342,747  8/1982  Lioteb et al. ............. 424/535
4,970,072  11/1990  Honda et al. ............. 424/535

FOREIGN PATENT DOCUMENTS 334776  9/1989  European Pat. Off. .
2617049  12/1988  France .
2733851  2/1978  Germany .

*Primary Examiner*—Jean C. Witz
*Attorney, Agent, or Firm*—Walter H. Schneider

[57] ABSTRACT

Pharmaceutical and/or dermocosmetic compositions containing equine colostrum, optionally in admixture with milk.

3 Claims, No Drawings

PHARMACEUTICAL AND DERMOCOSMETIC COMPOSITIONS CONTAINING EQUINE COLOSTRUM

The present invention refers to pharmaceutical, dermatological and cosmetic compositions containing equine colostrum optionally in admixture with equine milk or derivatives of equine colostrum or milk.

In the following description, the term "equine" preferably refers to horses although other equine species can be used as sources of colostrum (or milk) according to the invention.

Colostrum is defined according to the invention as the mammary secretion occurring in the period starting from some days before delivery until some days after delivery, characterized by an immunoglobulin content of at least 1000 mg/dl. In certain phases of the secretion, this content may be remarkably higher.

The pharmaceutical and/or dermocosmetological and cosmetic compositions of the invention contain therefore either equine colostrum as above defined or mixtures of colostrum and milk, in weight ratios ranging from 1:10 to 3:1, preferably from 1:9 to 2:1.

It has been found that the compositions of the invention, when topically applied on the skin, are particularly effective in the treatment of burns (caused by fire or sunlight), contact lesions (caused by jelly fishes or, generally by vescicant agents), of cutaneous diseases such as acne, seborrhoic dermatitis, irritations, dyscheratosis and dysmetabolic, dyspepsic forms, such as vascular cutaneous dystrophy, keratinization defects (psoriasis, ichtyosis), chronic photodamages, atopic dermatitis, senile itching, photoerythema and other common dermatological diseases.

According to the invention, equine colostrum and milk may also be formulated, in the above specified ratios, into cosmetic compositions having anti-burn, anti-lines, antiaging, moisturizing, protective, tensio-distensive, tonic, anti-relaxant, smoothing, anti-irritant, emollient, decongestionant, sun filtering, bleaching, lenitive sebum normalizing activities, repairing activity of damages by sun or radiant rays or generally by physical a chemical damages.

Thanks to their lenitive and anti-irritant action, the compositions of the invention may be effectively used, for instance, in cases of irritation of infants or children's skin caused by diapers, irritation after shave, and in all cases of irritation caused by atmospheric agents (sun, wind, cold etc).

Thanks to their tonic, distensive action on wrinkles, the compositions of the invention may be effectively used for the treatment of aging processes of the skin (antiaging action) caused both by physiological and by exogenous causes, such as noxious UV radiations, atmospheric agents, pollution etc. Thanks to their nutritive and sebumnormalizing action, the compositions of the invention may also be used in the treatment of diseases of the scalp and of hair, particularly of seborrhoic dermatitis and consequent alopecia; dandruff; fragility, dryness of the hair and split hairs due to decoloration or perm processes or the like.

The compositions of the invention are also useful for the prevention and treatment of cellulitis, couperouse and hair loss and, because of their healing and antiallergic action, for the treatment of burns, erythemas etc.

Examples of compositions of the invention comprise creams, lotions, tonic lotions, emulsions, ointments, gels, masks, foams, milks, detergent milks, aspersory pourders, sun- and after-sun creams, oils, shampoos, hair conditioners, packs lipsticks, after-shave creams and lotions, and the like.

The compositions of the invention typically contain from 1 to 50% by weight of equine colostrum (or mixtures thereof with equine milk in the above specified ratios) according to the intended uses, with suitable excipients and adjuvants.

Formulations consisting of pure equine colostrum (distributed, for instance, in vials or bottles) may also be provided.

Extractive or semi-synthetic derivatives of colostrum may also be used.

Moreover, the compositions of the invention may also optionally contain other active agents, having complementary or anyhow useful activity, such as anti-inflammatory, antibacterial, moisturizing, emollients, healing, repairing agents such as, for instance: Hedera elix, Centella asiatica, borage, calendula, sage, rosemary, vegetable oils, pineapple, sea weeds, papaya, blackberry, domestic chestnut, red vine, malva, jaluronic acid, elastine, collagene, hamamelis, wheat germ, carrot, green clay, thymus, propolis, etc.

The administration route and frequency will depend of course on the kind of formulation and of the desired effect but generally will be those typical for the kind of used formulations (creams 1 to 3 times a day; aftershave after each shaving; beauty mask once or more times a week; anti-irritating creams after each diaper change; shampoo and balsam once or more times a week and so on).

Equine colostrum or milk can be used either fresh, e.g. immediately after milking, or in lyophilized or spray-dried form.

For certain applications, sterility of the formulation may be a necessary requisite; in this case, colostrum or milk may be subjected to gamma rays sterilization without alteration of their characteristics. Equine colostrum can be frozen for its long-term preservation and thawed before its formulation in the final administration forms.

The compositions of the invention may also contain conventional excipients usually used in the preparation of pharmaceutical and cosmetic formulations, such as thickening agents, emulsifiers, detergents, sufactants, preserving agents, hair-conditioners, parfumes, etc.

The formulations of the invention have been clinically tested in a variety of conditions. The results are reported hereinafter.

Acne. Twelve 16–27 years old patients, affected by seborroic acne, were treated twice a day with topical application of cream containing 30% of horse colostrum in hydrosoluble base. In each case, the cutaneous lesions completely disappeared and restitutio ad integrum of the cutis took place within 6–12 days.

Contact lesions. Five cases of cutaneous lesions with contact vesicles (jelly-fish) were topically treated with two applications, at 12 hours intervals, of a cream containing 20% horse colostrum and 10% horse milk in hydrosoluble base, also containing peppermint and benzocaine. Pain immediately disappeared and the lesions recovered within 24 hours.

Sun burns. Thirty patients affected by sun burns with hyperthermia were treated twice a day with the same cream as used for contact lesions. Pain always immediately disappeared, with decrease of the cutaneous tension within 24 hours, followed in the subsequent days by normal sun-tan without desquamation. (Children were treated with the same cream, containing camomille extract instead of peppermint).

Fire burns Six cases of 2° degree fire burns and two of 3° degree burns were treated with the same cream and modalities as for sun burns. Again, pain disappearance was very fast and the complete restitutio ad integrum of epithelium occurred with one week.

Atopic dermatitis. Seven patients affected by atopic dermatitis of medium degree, were treated with 20% emulsion of equine colostrum twice a day for 30 days. 10 Healthy subjects were treated analogously as a control group. The treatment turned out to be well tolerated also on dermatitic cutis and to be endowed with emollient, lenitive, anti-inflammatory activities higher than that of commonly available emulsions. No cases of sensitization or sideeffect have been reported. The dryness of the skin was considerably reduced together with decrease of erythema and itching.

Ulcerative cutaneous lesions. Ten patients affected by cutaneous ulcerative lesions following to impairment of blood perfusion of primitive (vasculopathic) or secondary origin were treated twice a day for 20 days with a liposomial gel containing 20% of horse colostrum. No phlogistic effect occurred upon application of the gel. The completely or partially impaired healing processes improved, starting from the third day of treatment in 7 patients. A significant repair of the cutaneous lesion occurred in most cases.

The following examples further illustrate the invention.

| Contents: Composition: | |
|---|---|
| Example 1 | |
| Body cream | |
| Horse Colostrum | 3% |
| Horse Milk | 20% |
| Maize Germ Oil | 10% |
| Karité Butter | 10% |
| Sodium Lactate | 2% |
| Glycerol | 2% |
| Water | q.s. |
| Example 2 | |
| Face cream | |
| Horse Colostrum | 10% |

| Contents: Composition: | |
|---|---|
| Horse Milk | 20% |
| Squalene | 10% |
| Maize Germ Oil | 10% |
| Karité Butter | 10% |
| Sodium Lactate | 2% |
| Water | q.s. |
| Example 3 | |
| Anti-ulcer and anti-burn cream | |
| Horse Colostrum | 20% |
| Horse Milk | 10% |
| Beeswax | 10% |
| Maize Germ Oil | 10% |
| Zinc oxide | 7% |
| Panthenol | 3% |
| Water | q.s. |

I claim:

1. A composition for use in the topical treatment of skin disorders and injuries comprising as the principal active ingredient equine colostrum having an immunoglobulin content of at least 1000 mg/dl, or a mixture of said equine colostrum and equine milk in a ratio of 1:10 to 3:1 by weight, in admixture with suitable excipients and adjuvants, said principal active ingredient being present in an amount of 1.0% to 50% by wt.

2. A composition according to claim 1 in which the mixture of equine colostrum and equine milk is present in a ratio of 1:9 to 2:1.

3. A method of treating skin disorders and injuries which comprises applying directly to the area of the skin disorder or injury a composition according to claim 1.

* * * * *